United States Patent [19]

Palacci

[11] Patent Number: 5,842,859
[45] Date of Patent: Dec. 1, 1998

[54] INDICATING DEVICE AND A METHOD FOR MARKING OUT AND FORMING ONE OR MORE ATTACHMENT POINTS FOR A FIXTURE IN AN AREA OF THE HUMAN BODY, PREFERABLY THE JAW

[75] Inventor: Patrick Palacci, Marseilles, France

[73] Assignee: Nobel Biocare AB, Goteborg, Sweden

[21] Appl. No.: 902,905

[22] Filed: Jul. 30, 1997

Related U.S. Application Data

[63] Continuation of Ser. No. 449,906, May 25, 1995, abandoned.

[30] Foreign Application Priority Data

May 31, 1994 [SE] Sweden .................................. 9401858

[51] Int. Cl.⁶ ...................................................... A61C 19/04
[52] U.S. Cl. .................................. 433/72; 433/75; 433/76
[58] Field of Search ................................... 433/72, 75, 76, 433/173, 174, 175, 176

[56] References Cited

U.S. PATENT DOCUMENTS

| | | |
|---|---|---|
| 4,251,210 | 2/1981 | Weissman . |
| 4,260,383 | 4/1981 | Weissman .................................. 433/76 |
| 4,289,848 | 9/1981 | Miller et al. .............................. 433/72 |
| 5,055,042 | 10/1991 | Jansen ...................................... 433/76 |
| 5,208,845 | 5/1993 | Gelb . |
| 5,484,285 | 1/1996 | Morgan et al. ............................ 433/72 |

FOREIGN PATENT DOCUMENTS

94/00073   1/1994   WIPO .

*Primary Examiner*—John S. Hilten
*Attorney, Agent, or Firm*—Pollock, Vande Sande & Priddy

[57] ABSTRACT

A method and an indicating device for determining a location of a hole to be used as an attachment point for a fixture or fixture part on an area of the human body are disclosed. The indicating device comprises a bearing part which is adapted to be received in an existing hole and a protruding part interconnected with the bearing part and extending above the existing hole when the bearing part is inserted into the existing hole. At least one indicating part is interconnected with the protruding part and has a free end extending away from the existing hole, where a location of the new hole to be used as an attachment point is established at a position substantially adjacent to an exterior surface of the free end of the indicating part.

21 Claims, 3 Drawing Sheets

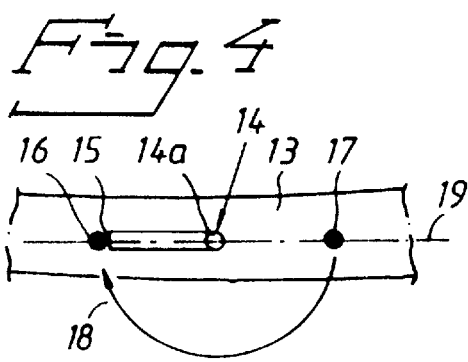
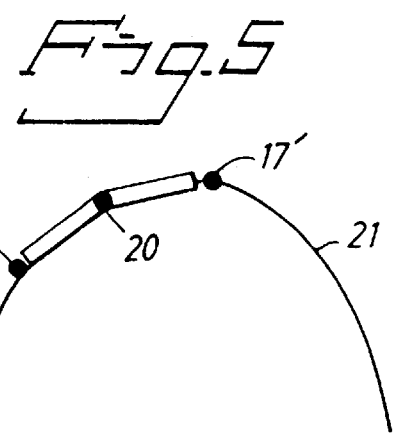
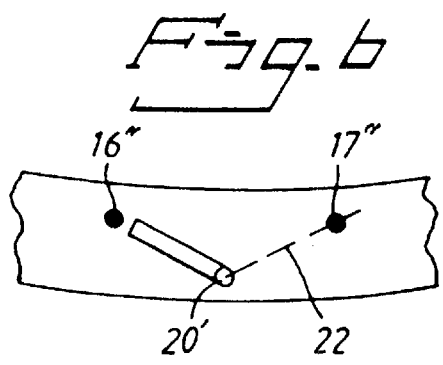
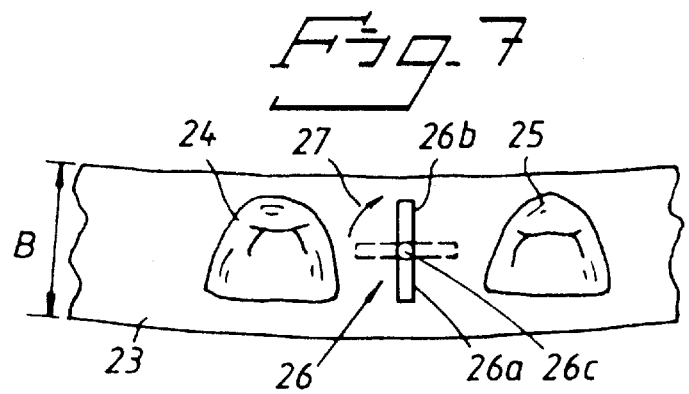
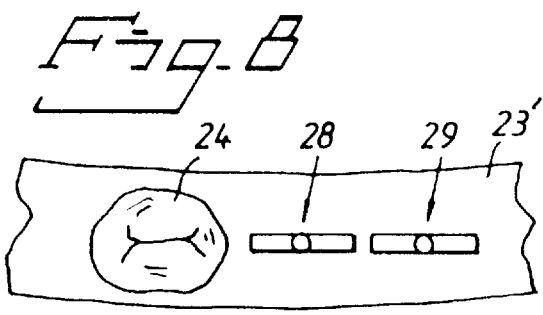
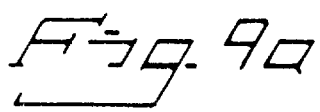
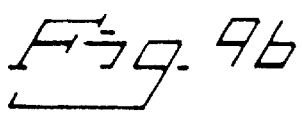
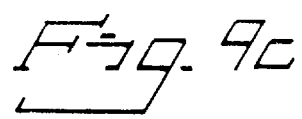
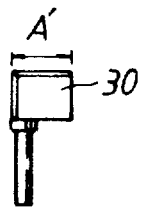
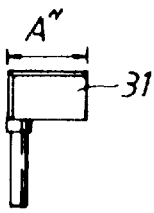
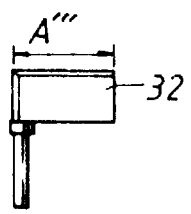

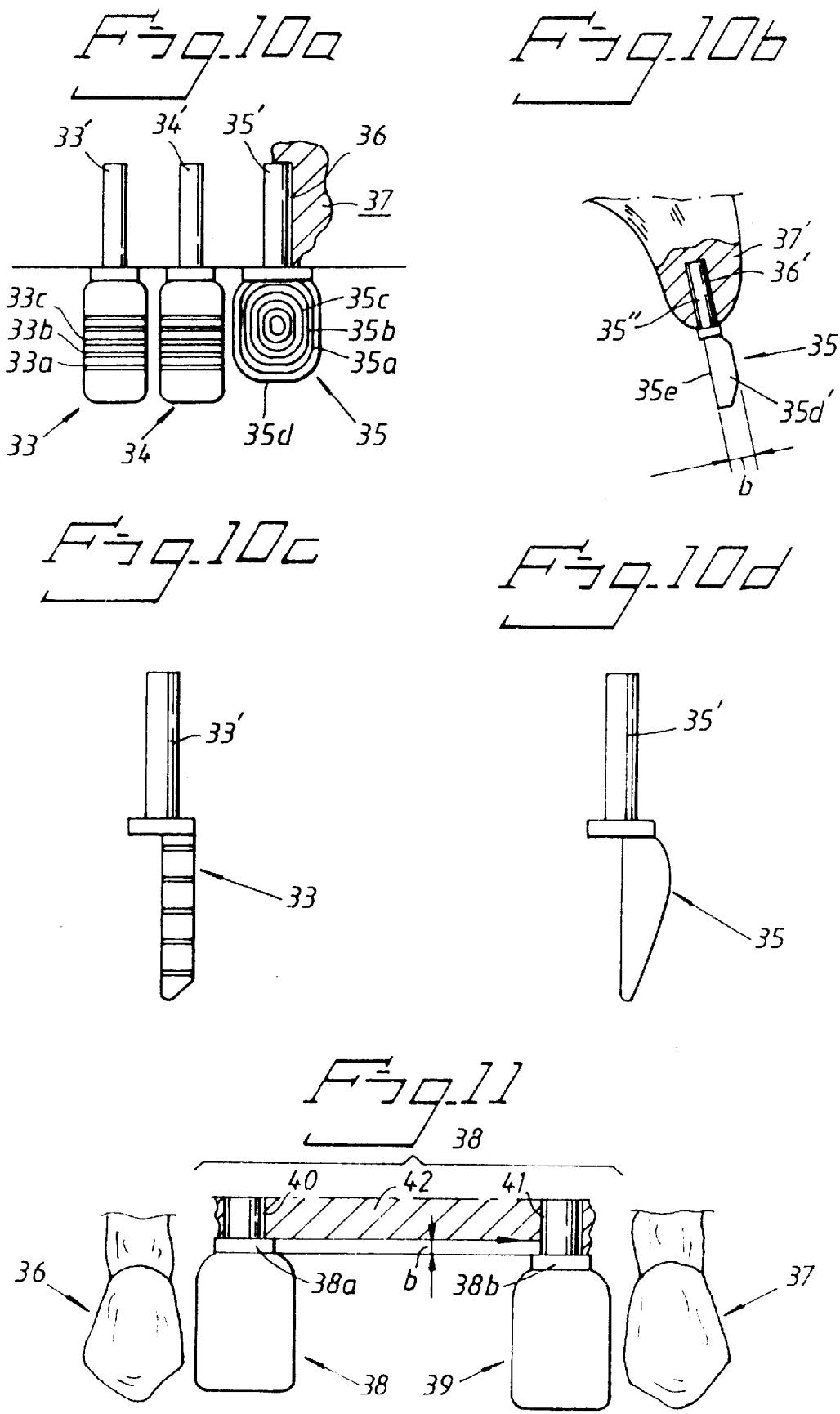

INDICATING DEVICE AND A METHOD FOR MARKING OUT AND FORMING ONE OR MORE ATTACHMENT POINTS FOR A FIXTURE IN AN AREA OF THE HUMAN BODY, PREFERABLY THE JAW

This application is a Continuation of U.S. patent application Ser. No. 08/449.906, filed May 25, 1995 now abandoned.

TECHNICAL FIELD

The present invention relates to an indicating device for marking and forming one or more attachment points for one or more fixtures on an area of the human body, preferably in the jaw/dentine. The device can be fitted into a receiving hole, here called the first receiving hole (drill hole), in which it bears via a bearing part and from which it protrudes above the area of the human body via a protruding part. The invention also relates to a method which provides for the indicating function.

BACKGROUND OF THE INVENTION

When installing dental implants, the positioning of the fixture is extremely important to obtain a good aesthetic and functional result. The positioning of the fixture to a large extent determines the choice of prosthetic components. In order to provide guidance for the surgeon during the installation of a fixture, various types of so-called surgical guide rails have traditionally been used. These guide rails need to be produced under laboratory conditions and can be made in a number of different designs. As aids during the surgical intervention it is also possible to use so-called directional sensors which indicate the inclination of the fixture to be fitted or the fixture attachment point.

Known directional sensors have a considerable disadvantage in that they only indicate inclination of the fixture to be fitted or fixture attachment point but do not provide any information on, for example, the horizontal distance to the next seat/attachment point. The invention aims to solve this problem, among others.

There is also a requirement, in conjunction with the formation of seat holes, to facilitate the formation of the holes or the drilling. The invention solves this problem since the indicating device in question can serve as a support during the formation of holes.

There is a requirement to combine several indicating functions within the same device or in a common system and, in conjunction with surgical interventions, to offer aids which provide references with respect to both vertical and horizontal distances and also with respect to the state of parallelism. The invention also solves this problem.

There is thus a requirement to optimize in a simple manner the height of the respective fixture/fixture part. This is made possible according to the invention by height markings. In addition, it is desirable to obtain indications on the labial angle and to acquire information on how the final product will be able to be fitted in the space or spaces in question in, or on, the dentine/jaw. This matter, too, is solved by the present invention. It provides various indications of distance and inclination by using technically precise and simple aids in the form of one or more devices which, in the last-mentioned case, can form part of a system. The invention also solves this problem. Thus, possibilities are afforded for simple volume indications for the replacement parts/ prosthetic components in question.

The use of previously employed surgical guide rails which need to be produced and used under laboratory conditions can also be dispensed with by means of the invention.

It is also desirable to offer simplified methods for forming holes for fixtures or fixture attachment points in, for example, the human jaw. The invention also solves this problem too.

SUMMARY OF THE INVENTION

The feature which may principally be regarded as characterizing a device according to the invention is that the protruding part mentioned in the introduction supports an indicating section, by means of which distances to one or more neighboring attachment points for one or more fixtures can be determined.

In a preferred embodiment, the indicating section has one or more surface position markings by means of which the height above the dentine or equivalent can be determined. In a preferred embodiment, the indicating device comprises a rod-shaped part which can be pushed into the first receiving hole. The preferred embodiment also includes a part which is angled in relation to the rod-shaped part and forms the indicating section. With its free end surface/edge, the angled part indicates the position of the respective desired attachment point in relation to the receiving hole which itself also forms an attachment point for a fixture or fixture part.

The indicating section or the angled part can have the shape of a flag, rectangle, or square which is integrated with, or connected to, the protruding part. The bearing and protruding parts of the indicating device as well as the indicating section, or the flag-shaped part can preferably be rotated together or reciprocally to allow the indicating section, or the flag-shaped part, to rotate to different angular positions in relation to the longitudinal direction of the protruding part, thereby permitting optimal adaptation of the respective attachment point for the respective fixture or fixture part.

The indicating section, or flag-shaped part, is arranged to provide support for the instrument in question, for example a drill, upon formation of a second receiving hole in the dentine or equivalent. The second hole constitutes a seat for the attachment point of the fixture or fixture part in question. The state of parallelism between the longitudinal axes of the first and second holes can thus be determined.

In a preferred embodiment, the indicating device can be applied in the first receiving hole, pivoted in the applied position for measuring in the optimal lateral distance to the second receiving hole, and thereafter pivoted again for measuring in a third receiving hole, etc. The indicating device can, in addition, be provided with a number of height markings for setting the optimal height of the fixture or fixture part above the dentine or equivalent. The indicating section can form the protruding part and can consist, for example, of a rectangular element associated with the bearing part.

Volume references can also be obtained with the aid of the indicating device. In one embodiment, the indicating device is designed as a semispherical body with a plane surface for volume markings, which in this case can consist of markings in the form of rings. The increasing volume of the body is indicated by decreasing ring sizes and vice versa.

The indicating device can form part of a system of indicating devices, in which a first type of indicating device is used for indicating essentially horizontal optimal distances between attachment points for one or more fixtures. A second type of indicating device indicates essentially vertical optimal heights for the fixture above, for example, the dentine in question. A third type of indicating device indicates the optimal volume-related (labial) shaping of the fixture or replacement part in question. One or two, or all types, of indicating devices can in this case be present in various sizes and/or values for the respective indication.

According to the invention, a method is also proposed which uses the indicating device in accordance with the above. The method includes introducing the indicating device into a first receiving hole via its bearing part, and in the position or positions of one or more neighboring second receiving holes being determined with the aid of one or more indicating sections on the indicating device in question. In one embodiment of the method, the indicating section or sections is/are turned about the longitudinal axis of the first receiving hole for marking the positions for the two or more second receiving holes. The height of the respective fixture or fixture part is determined with the aid of one or more height markings on the indicating device or the indicating section. A volume reference can also be obtained using the inventive indicating.

ADVANTAGES OF THE PRESENT INVENTION

By means of the present invention above, the positioning of the fixtures concerned, and assessments of the appearance of the respective implant, can be considerably facilitated. Indicating devices with different distance markings permit pre-planning of different fixture positions in a simple manner. This indicating principle can be used independently of the shapes of the dentine and jaw and of the dental status of the patients in question.

BRIEF DESCRIPTION OF THE DRAWINGS

A presently proposed embodiment of a device and a method according to the invention will be described with reference to the attached drawings, in which:

FIG. 4 shows, in a horizontal view, the rotatability of an indicating device according to FIGS. 1–3 for marking out two positions for second receiving holes;

FIG. 5 shows, in a horizontal view, the rotatability of the indicating device in relation to a curved shape;

FIG. 6 shows, in a horizontal view, the indicating device being rotatable in relation to a tripod shape;

FIG. 7 shows, in a horizontal view, the use of an indicating device of a type other than that in FIGS. 1–6, which illustrated indicating device is used for indicating the volume of a planned replacement part;

FIG. 8 shows, in a horizontal view, two indicating devices according to FIG. 7 arranged alongside one another;

FIGS. 9a–9c show, in vertical views, indicating devices according to FIGS. 1–6 with different lengths of indicating sections;

FIGS. 10a–10d show, in vertical views, indicating devices with height markings and volume markings; and FIG. 11 shows, in a vertical view, the height adjustment for fixture attachment points in relation to teeth in dentine.

DETAILED DESCRIPTION OF THE INVENTION

Figure 1:
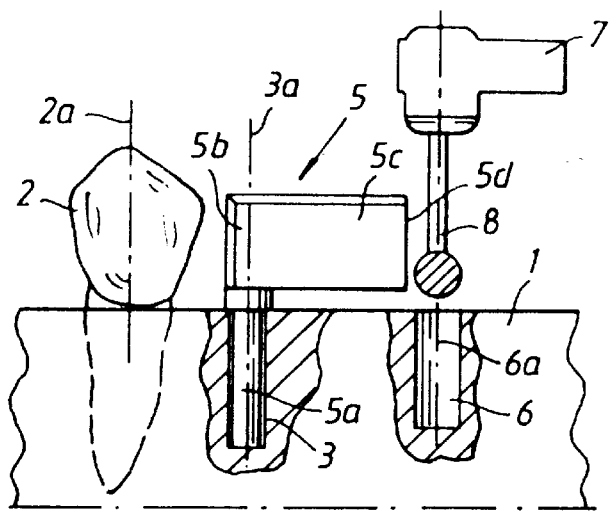
FIG. 1 shows, in a vertical and partial cross-sectional view, the use of an indicating device in dentine, the indicating device being positioned in relation to a tooth, and an attachment hole for a fixture being marked out and a drill instrument being applied.

In FIG. 1 the jawbone of a human is indicated by 1. A tooth is indicated by 2 and the longitudinal axis of the tooth by 2a. A first receiving hole or drill hole 3 has been made in the dentine to the side of the tooth. The vertical axis/ longitudinal axis of the drill hole is indicated by 3a. An indicating device is positioned in the first drill hole 3 which indicating device bears in the hole 3 via a bearing part 5a and has a part 5b protruding from the hole 3 as well as an indicating section 5c.

In this embodiment, the parts 5b and 5c form a common part. In the case shown, the parts are formed as an essentially plate-shaped and rectangular part, which can be considered as a flag-shaped part. The indicating member can of course have other shapes.

The part 5c has a free end surface 5d. The end surface 5d constitutes an indication to the surgeon or dentist where he or she should drill a second receiving hole 6. The longitudinal axis of the second hole is indicated by 6a. A drill instrument is indicated by 7, and a marker drill associated therewith by 8. In the present case the holes are assumed to be essentially parallel and vertical. The longitudinal axis 2a of the tooth is also parallel with the axes 3a, 6a.

Figure 2:
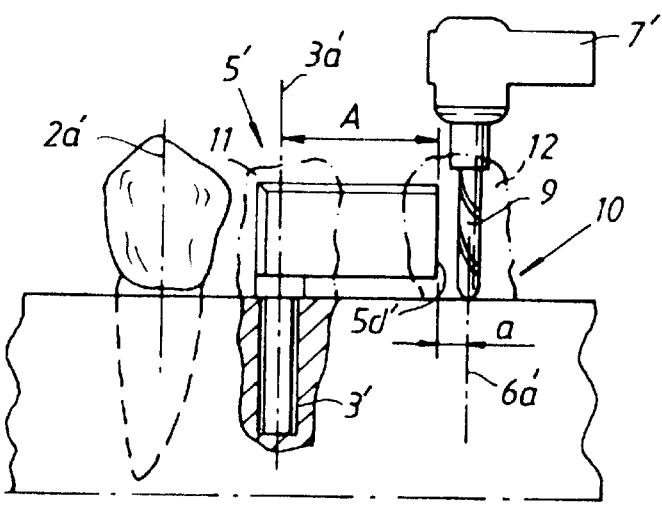
FIG. 2 shows, in a vertical view, the situation according to FIG. 1, but in which another type of drill has been applied in the drill instrument, and in which the shapes of the fixtures have also been shown.

In FIG. 2 the drill instrument 7' is shown with a starting drill 9. During the drilling work, the end surface or side surface 5d' can serve as a support for the drill. The indicating device 5' indicates to the surgeon a A, which distance represents an optimal distance from the longitudinal axis 3a' to the vicinity of position 10.

The drawing shows a distance "a" between the end surface 5d' and the longitudinal axis 6a' of the second hole. The distance a can be between zero and a few mm. The recess 3' will, in this case, constitute an attachment hole for a first fixture which is symbolized partially in the drawing by 11. This fixture is built upon in a known manner with material for building up the actual replacement part (tooth, dental bridge, among others).

In a corresponding manner, the second receiving hole will constitute an attachment hole for a second fixture which is symbolized by 12 in FIG. 2 and which represents a foundation on which the finished replacement part is built. The fixtures 11 and 12 can be separate. Alternatively, 11 and 12 can form fixture parts which are included in the same prosthetic reconstruction. In FIG. 2 the axis of the tooth is indicated by 2a'.

Figure 3:
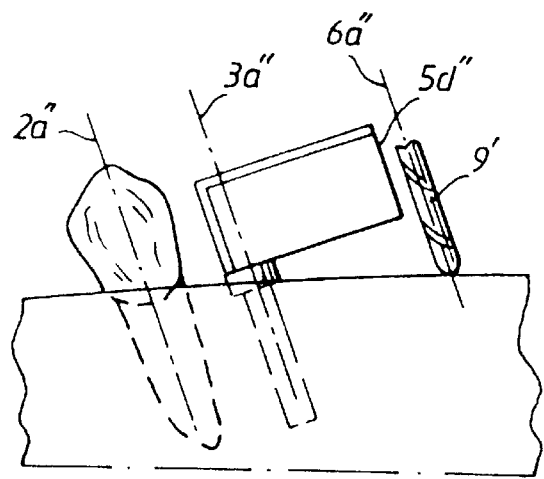
FIG. 3 shows, in a vertical view, the application of an indicating device in relation to an inclined tooth in the jawbone in question.

FIG. 3 shows that the state of parallelism can exist between the axes 2a", 3a" and 6a" even when the axes are steeply inclined. In this case, too, the end surface 5d" can constitute a support for the drill 9'. Alternatively, one or all of the axes can be nonparallel.

FIG. 4 shows a view from above of the dentine 13 and of an indicating device 14. The indicating device has a shape corresponding to the above and can be pivoted about its common bearing and protruding part when it is applied in its first bearing hole, hole 3 shown in FIG. 1. In this case, the end surface of the indicating device is shown by 15, surface 5d shown in FIG. 1. The indicating device can be pivoted to indicate the positions 16 and 17 for two second receiving holes for implants/fixtures. The pivotability is shown by an arrow 18. In FIG. 4, the receiving holes are placed along an essentially straight line 19.

FIGS. 5 and 6 show that the three receiving holes 16', 17' and 20, and 16", 17" and 20', respectively, can be arranged along a curve or, respectively, form a tripod shape 22.

The indicating device can also be used as a volume indicator in accordance with FIGS. 7 and 8. In FIG. 7, dentine is shown from above by 23 together with two teeth 24 and 25. The indicator 26 in this case has two wings 26a, 26b which protrude from either side of the common bearing and protruding part 26 which is fitted in a bearing hole in accordance with the above. A 90° pivoting in the direction of the arrow 27 provides an indication for the replacement part to be fitted in the width direction B of the dentine 23.

FIG. 8 shows the use of two indicating devices which provide the user with volume information in relation to the fixture shape.

FIGS. 9a, 9b and 9c show different lengths A', A", A'" of the distance-indicating sections of the parts 30, 31, and 32, respectively. The parts 30, 31, and 32 have a function and shape corresponding to those of the indicating member 5 in FIG. 1.

FIG. 10a shows examples of height indicators 33, 34, and volume indicator 35. Each height indicator is designed with horizontal, or lacuna markings 33a, 33b, 33c etc. The volume indicator is provided with ring markings 35a, 35b, 35c, etc. An increasing volume, or thickness at the rear of the semispherical or half-cup-shaped body 35d is indicated by decreasing ring sizes, or vice versa. The surface which exhibits the ring markings, which is the surface coinciding with the plane of FIG. 10a, is preferably flat. The indicating devices are designed, in a manner corresponding to the above, with bearing parts 33', 34' and 35', respectively, arranged in recesses 36 in dentine 37.

FIG. 10b shows the body 35d' with the bearing part 35" arranged in a recess 36' in the dentine 37'. The volume or thickness b is represented by ring markings corresponding to 35a, 35b, 35c in FIG. 10a. The flat surface is represented by 35e.

FIGS. 10c and 10d show examples of how the indicating devices 33, 34 and, respectively, 35 can appear in side view.

In FIG. 11 two teeth are represented by 36 and 37. In the space 38 between the teeth the height indicating devices 38 and 39 in accordance with the above are arranged in bearing recesses 40 and 41 in the dentine 42. A distance b can be determined by comparing the height markings 38a and 38b, and it is possible to decide whether an adjustment in height or drill depth of the holes 40, 41 should or should not be made.

The invention is not limited to the embodiment shown hereinabove by way of example, but instead can be subject to modifications within the scope of the following patent claims and the inventive concept.

I claim:

1. An indicating device for determining a location of a hole to be used as an attachment point for a fixture or fixture part on an area of the human body, said indicating device comprising:
   a bearing part adapted to be received in an existing hole;
   a protruding part interconnected with said bearing part and extending above said existing hole when said bearing part is inserted into said existing hole; and
   at least one indicating part interconnected with said protruding part at one end thereof and having a second free end extending away from said existing hole, said free end defining a location of said hole to be used as an attachment point at a position adjacent to and outside an exterior surface of said free end of the indicating part.

2. An indicating device according to claim 1, wherein said indicating part includes a first end interconnected with said protruding part and a second, free end laterally spaced from said first end.

3. An indicating device according to claim 1, wherein the indicating part is a flat rectangular plate, one vertical edge thereof defining said free end and providing a one-direction drill support.

4. An indicating device according to claim 1, wherein said indicating part includes height markings for determining height above the area of the human body.

5. An indicating device according to claim 1, wherein said bearing part comprises a rod-shaped part insertable into an existing hole, and said indicating part comprises an indicating section having a longitudinal axis that is angled with respect to a longitudinal axis of the rod-shaped part, said indicating section having a free end surface for indicating a position for a neighboring hole relative to the existing hole.

6. An indicating device according to claim 5, wherein said indicating section comprises a flag-shaped or rectangular part integrated with or connected to the protruding part.

7. An indicating device according to claim 5, wherein said bearing part, said protruding part, and said indicating section are rotatable together to permit the indicating section to rotate to different angular positions relative to the longitudinal axis of the protruding part, thereby indicating possible positions of neighboring holes.

8. An indicating device according to claim 5, wherein said bearing part, said protruding part, and said indicating section are reciprocally rotatable to permit the indicating section to rotate to different angular positions relative to the longitudinal axis of the protruding part, thereby indicating possible positions of neighboring holes.

9. An indicating device according to claim 5, wherein said indicating section provides support in one direction for an instrument or drill for formation of a neighboring hole, said indicating section permitting formation of the neighboring hole parallel to the existing hole.

10. An indicating device according to claim 5, wherein said indicating device is received by the existing hole and is pivotable in a first direction in the existing hole for measuring optimal distance to a first neighboring hole and is pivotable in an opposite direction in the existing hole for measuring optimal distance to a second neighboring hole.

11. An indicating device according to claim 4, wherein said protruding part and said indicating part are integral and form a unitary body comprising a rectangular element associated with the bearing part.

12. An indicating device according to claim 11, wherein said protruding part and said indicating part comprise a semispherical or half-cup-shaped body including markers for marking a volume of the semispherical or half-cup-shaped body.

13. An indicating device according to claim 12, wherein said markers comprise rings on a flat marking surface, and wherein a decreasing ring size indicates an increasing volume at the rear of the semispherical or half-cup-shaped body.

14. An indicating device according to claim 1, wherein said indicating device provides a portion of a system of indicating devices including a first device that indicates horizontal distances and parallelism between longitudinal axes of holes, a second device that indicates vertical heights for fixtures, fixture parts, or replacement parts to be arranged in the hole, and a third device that indicates a volume-related shaping of the fixtures, fixture parts, or replacement parts, wherein at least one indicating device may be present in various sizes and/or values for a respective indication.

15. An indicating device according to claim 1, wherein said device is for verifying positioning of existing holes and positioning neighboring holes are in a human jaw.

16. A method for establishing a location of at least one new hole to be used as an attachment point for a fixture or fixture part on an area of a human body, said method comprising the steps of:

forming a first receiving hole in an area of a human body;

introducing a bearing part of an indicating device into the first receiving hole; and utilizing at least one indicating part, interconnected with the bearing part at one end thereof and having a free end extending away from said existing hole, establishing a location of said new hole by locating said new hole at a position substantially adjacent and outside an exterior surface of said free end of the indicating part.

17. A method according to claim 16, further comprising the step of:

rotating the bearing part in the hole, thereby turning the indicating section for marking positions for establishing in the area of a human body additional holes providing attachment points for fixtures or fixture parts.

18. A method according to claim 16, further comprising the step of:

determining with at least one marking on the indicating part of the indicating device a height of a fixture or fixture part to be inserted in to the hole.

19. A method according to claim 16, further comprising the step of:

determining with a volume-indicating device on the indicating part of the indicating device a volume of a fixture or fixture part to be inserted in to the hole.

20. A method according to claim 16, wherein said at least one hole is formed in a human jaw.

21. A method according to claim 16 further including the step of supporting a drill along said exterior surface at said free end of the indicating part during drilling of the new hole.

* * * * *